United States Patent [19]

Thomas et al.

[11] Patent Number: 5,099,532
[45] Date of Patent: Mar. 31, 1992

[54] ABSORBENT BED PAD WITH STABILIZING STRIPS

[75] Inventors: Richard M. Thomas, Raleigh; Roger P. Sload, Spring Hope, both of N.C.

[73] Assignee: The Sewing Source, Inc., Spring Hope, N.C.

[21] Appl. No.: 671,194

[22] Filed: Mar. 18, 1991

[51] Int. Cl.5 .......................... A47G 9/02; A61G 9/00
[52] U.S. Cl. .................................. 5/484; 5/502; 604/385.1
[58] Field of Search ............... 5/484, 482, 500, 502; 604/385.1, 383, 358

[56] References Cited

U.S. PATENT DOCUMENTS

| | | | |
|---|---|---|---|
| 1,621,149 | 3/1927 | Blissitt . | |
| 2,222,782 | 11/1940 | Moses . | |
| 3,427,670 | 2/1969 | Nimoy . | |
| 3,670,345 | 6/1972 | Doll et al. . | |
| 4,045,833 | 9/1977 | Mesek et al. . | |
| 4,097,943 | 7/1978 | O'Connell | 5/484 |
| 4,173,046 | 11/1979 | Gallagher | 5/484 |
| 4,524,474 | 6/1985 | Svesson | 5/484 |
| 4,664,959 | 5/1987 | Dagenais et al. | 428/74 |
| 4,844,965 | 7/1989 | Foxman . | |
| 4,943,286 | 7/1990 | Armstead | 604/358 |
| 4,961,982 | 10/1990 | Taylor | 428/41 |

FOREIGN PATENT DOCUMENTS

286330  11/1988  Japan ................ 604/385.1

*Primary Examiner*—Alexander Grosz
*Attorney, Agent, or Firm*—Bell, Seltzer, Park & Gibson

[57] ABSTRACT

The pad has an upper cotton layer quilted to an underlying soaker layer formed of needle-punched nonwoven polyester fibers having good absorbency and wickability. A plurality of longitudinally and transversely extending stabilizing strips underlie the soaker layer. The strips are preferably formed of nylon fabric having a dry polymer coating which renders the fabric waterproof and heat-bondable. The pad also includes a lower layer formed of the same type of coated nylon fabric. The stabilizing strips are connected by stitching to the upper layer and the soaker layer of the pad, and are bonded to the pad's bottom layer. The bonding is effected by application of heat and pressure sufficient to effect melding of the coatings upon the stabilizing strips and the lower layer.

20 Claims, 1 Drawing Sheet

ABSORBENT BED PAD WITH STABILIZING STRIPS

FIELD OF THE INVENTION

This invention relates to bed pads of the type used to absorb urine, blood and/or other body fluids discharged by bedridden persons who are incontinent or have bleeding wounds, surgical incisions or the like. The invention more specifically relates to a pad of the foregoing type that is reusable and that can retain its desirable properties and functions even after being washed or laundered many times.

BACKGROUND OF THE INVENTION

One function of a bed pad of the above-noted type is to prevent or at least minimize soiling of the mattress and/or bed linens of the bed upon which the pad is used. Another important function of the pad is to enhance the comfort of the person lying upon the pad. The bedridden person's comfort is enhanced when the pad conducts the discharged fluid away from his or her body, and is also enhanced when the pad is substantially free from "lumps" or the like created by undesirable displacement of fibrous or other absorbent filling material within the pad. Lumps and the like are particularly likely to form in a reusable pad that is subjected to repeated laundering operations.

SUMMARY OF THE INVENTION

The present invention provides an absorbent bed pad that, while of a reusable type adopted to undergo repeated laundering, possesses the previously-noted desirable attributes, and other desirable benefits. The pad includes an upper layer of soft fabric material, an underlying "soaker" layer of absorbent fibers, a plurality of relatively long and narrow stabilizing strips underlying the soaker layer, and a liquid impervious layer underlying the foregoing layers and strips. The pad may also include a binder strip that encircles the periphery of the pad.

In a preferred embodiment of the pad, its upper layer, soaker layer and stabilizing strips are secured together by stitching, and the stabilizing strips are bonded to the pad's liquid impervious lower layer. Such bonding is preferably achieved by application of heat and pressure to dry thermoplastic polymeric coating material upon the confronting surfaces of the stabilizing strips and the lower layer of the pad.

BRIEF DESCRIPTION OF THE DRAWINGS

Other features of the invention will be apparent from the following description of a preferred embodiment thereof, which should be read in conjunction with the accompanying drawings in which.

DESCRIPTION OF THE PREFERRED EMBODIMENT

Figure 1:
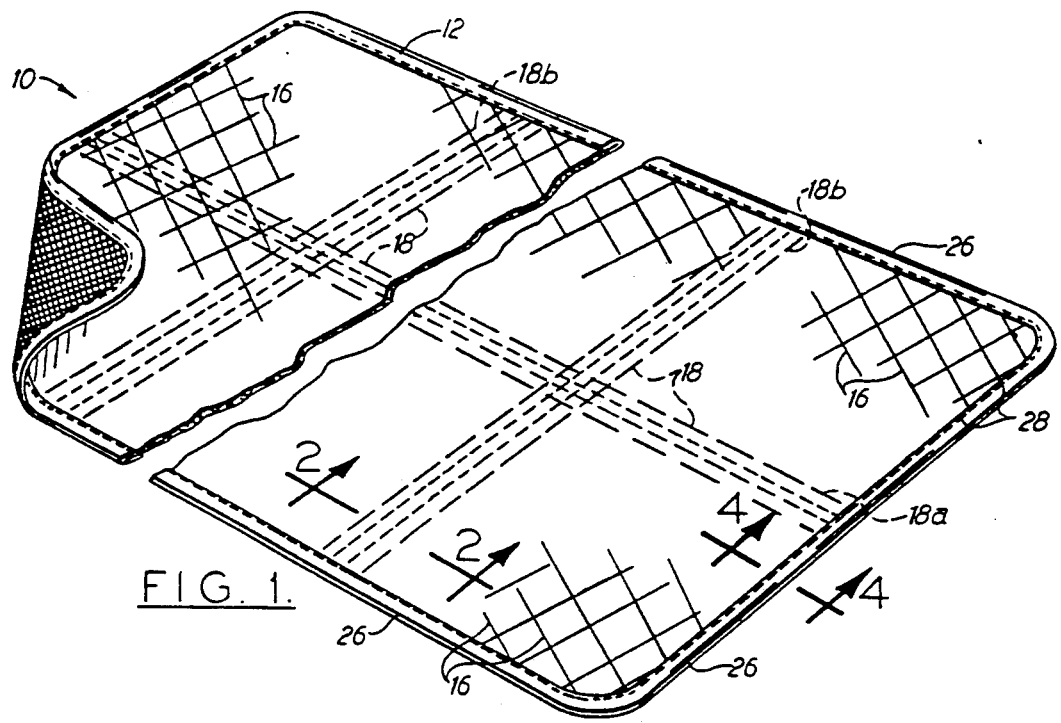
FIG 1 is a foreshortened top perspective view of an absorbent bed pad in accordance with the invention, a corner of the pad being partially folded over so as to also show part of the bottom thereof.

The absorbent bed pad identified in the drawings in its entirety by the numeral 10 includes an upper layer 12 formed of liquid pervious material, which preferably and illustratively is a soft cotton fabric. Upper layer 12 overlies a relatively thick coextensive "soaker" layer 14 comprised of needle-punched polyester or similar fibers that readily absorb and retain liquids, and have good wickability. The weight of layer 14 preferably is approximately nine ounces per square yard. Layers 12, 14 are secured together by quilting stitches 16, which preferably number approximately eight to ten per inch.

Figure 3:
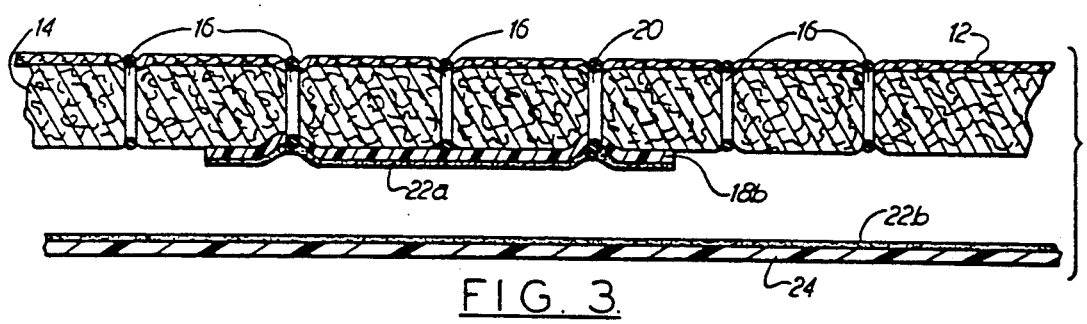
FIG. 3 is a view similar to FIG. 2, but showing the polymer coated lower layer of the pad in exploded relationship to the overlying part of the pad.
Figure 4:
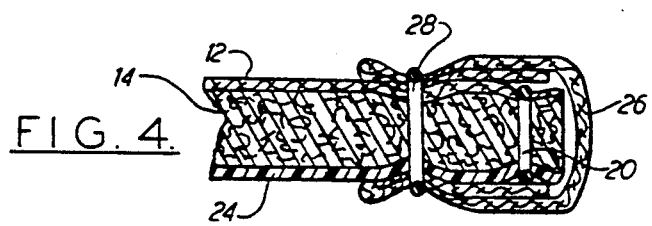
FIG. 4 is an enlarged fragmentary sectional view taken substantially along the lines and in the direction of the arrows 4—4 through an edge portion of the pad.

A plurality of relatively long and narrow stabilizing strips 18 are secured at spaced intervals to the undersurface of soaker layer 14 by stitches 20 that also extend through upper layer 12. The stabilizing strips 18 illustratively include a strip 18a that is located approximately centrally of the width of pad 10 and that extends along substantially its entire length. The strips 18 further include two strips 18b that extend perpendicularly relative to strip 18a, and in laterally spaced substantially parallel relationship to each other and to the opposite ends of pad 10, between the opposite sides of the pad. Each of the strips 18 preferably is formed of oxford cloth woven from 200 denier type 66 bright nylon yarn, having a thread count of about 60×50, and a weight in the range of approximately 2.7–3.3 ounces per square yard. The surface of the cloth constituting the lower surface of each strip 18 is coated with approximately 1.5–2.5 ounces (dry weight) per square yard of thermoplastic polymeric material, preferably polyether polyurethane. The coating renders the fabric liquid impervious and heat-bondable to a similarly constructed and coated fabric. The coating, which is identified in FIG. 3 of the drawings by the numeral 22a, preferably covers substantially the entire lower surface of each of the stabilizing strips 18.

Figure 2:
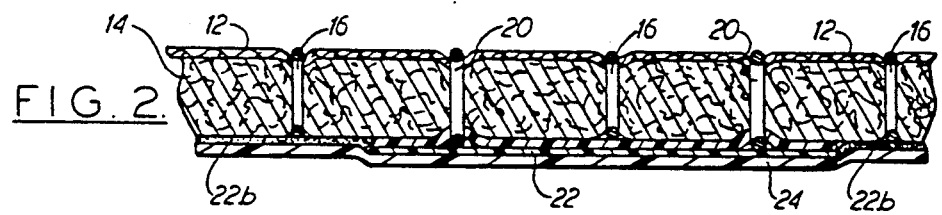
FIG. 2 is an enlarged fragmentary sectional view taken generally along the lines and in the direction of the arrows 2—2 through the pad of FIG. 1.

The remaining, lower layer 24 of pad 10 may be and illustratively is made of the same liquid impervious, heat-bondable, coated nylon cloth as that from which stabilizing strips 18 are formed. However, layer 24 is oriented such that its polyurethane coating 22b is upon and coextensive with its upper surface, rather than its lower surface. The confronting surfaces of stabilizing strips 18 and lower layer 24 are bonded together, preferably and illustratively throughout substantially the entire length and width of the strips. The bonding operation may be and preferably is accomplished without the use of any extraneous adhesive, by pressing the confronting coated surfaces of strips 18 and layer 24 together while heating them sufficiently to effect melding of the polyurethane coatings 22a, 22b thereon. The melded coatings, which are designated in FIG. 2 of the drawings by the numeral 22, provide a strip adhesion of approximately 25 psi between each strip 18 and layer 24.

An edge binding strip 26 encircles the periphery of the superimposed layers 12, 14 and 24 of pad 10. Strip 26, which may be and illustratively is formed of cotton fabric, assists in preventing escape of liquid from the edges of the pad, and strengthens such edges. The upper and lower sections of the strip are each preferably folded upon themselves to provide a double thickness. Single needle lock stitches (preferably approximately eight to ten per inch) 28 secure binding strip 26 and the peripheral sections of pad layers 12, 14 and 24 together.

Except adjacent its peripheral edges, lower layer 24 is free from needle holes that might possibly permit leakage of liquid through such layer. If desired, the binder strip might instead be formed of a material capable of being secured in place by bonding, rather than by stitches. This would further decrease the possibility of leakage of liquid from the pad 10 during use.

Pad 10 is highly durable, and is capable of withstanding a large number of laundering operations without loss of its structural integrity or comfort. In the latter regard, the formation of undesirable lumps or the like within soaker layer 14, by reason of "clumping" or other displacement of its fibers, is minimized since layer 14 is secured in place not only by stitching, but also by stabilizing strips 18.

While a preferred embodiment of the invention has been shown and described, this was for purposes of illustration only, and not for purposes of limitation, the scope of the invention being in accordance with the following claims.

We claim:

1. A reusable absorbent bed pad adapted to be laundered repeatedly, comprising:
   an upper layer of liquid pervious material;
   a soaker layer of liquid absorbent material underlying said upper layer;
   a plurality of relatively long and narrow stabilizing strips underlying said soaker layer;
   a lower layer of liquid impervious material underlying said stabilizing strips and said soaker layer, said stabilizing strips and said lower layer being bonded together;
   and securing means securing said stabilizing strips to said soaker layer and to said lower layer.

2. A pad as in claim 1, and further including an edge binding strip secured to the periphery of said pad.

3. A pad as in claim 2, wherein said edge binding strip is secured to said upper layer, said soaker layer and said stabilizing strips by stitching.

4. A pad as in claim 1, wherein said upper layer is formed of cotton fabric material.

5. A pad as in claim 4, wherein said soaker layer is formed of needle-punched nonwoven fibers.

6. A pad as in claim 5, wherein said stabilizing strips include at least a first strip and a second strip extending in a transverse relationship to each other.

7. A pad as in claim 6, wherein at least one of said stabilizing strips extends from one edge of said pad to another edge of said pad.

8. A pad as in claim 7, wherein said first and second stabilizing strips extend in substantially perpendicular relationship to each other.

9. A pad as in claim 8, wherein said stabilizing strips further include a third strip extending in generally parallel, laterally spaced relationship to one of said first and second strips.

10. A pad as in claim 9, wherein said lower layer is formed of fabric having a coating of polymeric material upon at least one side thereof.

11. A pad as in claim 10, wherein said fabric of said lower layer is nylon oxford cloth, and said coating is upon the upper side thereof.

12. A pad as in claim 11, wherein said stabilizing strips are secured along substantially the entire length thereof to said lower layer 13. A pad as in claim 12, wherein said stabilizing strips are secured to said lower layer by said coating of polymeric material.

14. A pad as in claim 13, wherein said stabilizing strips have a coating of said polymeric material upon the lower surfaces thereof, and said coating of polymeric material upon said stabilizing strips assists in securing said strips to said lower layer.

15. A pad as in claim 14, wherein said polymeric material is polyether polyurethane.

16. A pad as in claim 15, wherein said coating upon each of said strips and upon said lower layer has a dry weight within the range of approximately 1.5–2.5 ounces per square yard.

17. A pad as in claim 16, wherein said nylon fabric is formed of 200 denier type 66 bright nylon yarn and has a thread count of approximately $60 \times 50$.

18. A reusable absorbent bed pad adapted to be laundered repeatedly, comprising:
   an upper layer of liquid pervious material;
   a soaker layer of liquid absorbent material underlying and substantially coextensive with said upper layer;
   a plurality of stabilizing strips underlying said soaker layer;
   a lower layer of liquid impervious material underlying said stabilizing strips and said soaker layer;
   said stabilizing strips and said lower layer being bonded together.

19. A pad as in claim 18, and further including stitching securing said upper layer, said soaker layer and said stabilizing strips together.

20. A pad as in claim 18, wherein said stabilizing strips and said lower layer each have a coating of thermoplastic polymeric material thereon, and said bonding is effected by said thermoplastic polymeric material.

* * * * *